United States Patent [19]

Lardner

[11] Patent Number: 4,744,391

[45] Date of Patent: May 17, 1988

[54] FLOW CONTROL VALVE

[75] Inventor: George E. Lardner, Seminole, Fla.

[73] Assignee: Halkey-Roberts Corporation, St. Petersburg, Fla.

[21] Appl. No.: 867,238

[22] Filed: May 23, 1986

[51] Int. Cl.4 .............................................. F16K 31/50
[52] U.S. Cl. .................... 137/877; 128/685; 137/886; 251/122; 251/273
[58] Field of Search ................ 128/685; 137/886, 877; 251/122, 215, 273

[56] References Cited

U.S. PATENT DOCUMENTS

| 2,685,294 | 8/1954 | Gold et al. | 251/122 X |
| 2,934,061 | 4/1960 | Speelman | 128/685 |
| 3,255,775 | 6/1966 | Albro et al. | 251/215 X |
| 3,747,894 | 7/1973 | Pepper | 251/215 |
| 3,831,629 | 8/1974 | Mackal et al. | 137/843 |
| 4,072,171 | 2/1978 | Nakazawa | 128/685 X |
| 4,602,655 | 7/1986 | Mackal | 137/515 |

FOREIGN PATENT DOCUMENTS 2758894 8/1978 Fed. Rep. of Germany ...... 128/685

Primary Examiner—Gerald A. Michalsky
Attorney, Agent, or Firm—Dominik, Stein, Saccocio & Reese

[57] ABSTRACT

A flow control valve operable to bleed pressure from a pressurized source. The flow control valve includes an integral body, a bleed cap, a bleed valve element and a check valve assembly formed of a valve housing and a valve element.

3 Claims, 1 Drawing Sheet

FLOW CONTROL VALVE

BACKGROUND OF THE INVENTION

1. Field of the Invention

This invention relates to flow control valves operable to bleed pressure from a pressurized source. More particularly, this invention relates to flow control bleed valves having a check valve incorporated therein allowing pressurization of the pressure source.

2. Description of the Background Art

Presently, there exist many types of flow control valves operable to regulate the flow of a fluid into and out of a tank or other container. Basically, the more predominate type of flow control valve comprises a spring-loaded ball which is urged against a valve seat by means of a vented turn knob. During operation, rotation of the turn knob increases (or decreases) the space between the ball and the valve seat, thereby regulating the flow of fluid therethrough. These types of flow control valves work quite suitably and reliably. However, since each component part of the flow control valve requires machining and deburring, these valves are manufactured at a relatively high cost.

In many applications, it is desirable to incorporate a check valve into the flow control valve such that the flow of fluid in one direction is uninhibited, while the flow of fluid in the opposite direction is controlled. For example, in the medical field, it is almost universal practice to utilize a flow control/check valve in-line between the pump bulb and the inflatable cuff of a blood pressure monitor (sphygmomanometer). The check valve of a control valve of this nature allows the inflatable cuff to be freely inflated to a desired pressure by pumping of the pump bulb. After the cuff is suitably inflated to the desired constricting pressure about the patient's arm, the cuff is slowly deflated by slowly bleeding the pressure contained therein through the use of the flow control valve. Of course, many other applications exist which require the use of a flow control valve having a check valve incorporated therein.

Therefore, it is an object of this invention to provide an apparatus which overcomes the aforementioned inadequacies of the prior art devices and provides an improvement which is a significant contribution to the advancement of the flow control valve art.

Another object of this invention is to provide a flow control valve which is economical to manufacture and highly reliable in operation.

Another object of this invention is to provide a flow control valve composed of injection molded parts which do not require machining or deburring prior to assembly thereby reducing the cost of manufacture thereof.

Another object of this invention is to provide a flow control valve having a turn knob which, on rotation, variably controls the flow of fluid therethrough.

Another object of this invention is to provide a flow control valve having a check valve incorporated therein, allowing a tank or other container to be inflated to a pressurized state by means of the check valve and then slowly deflated to a depressurized state by means of the variable flow control valve.

Another object of this invention is to provide a flow control valve operable as a bleed valve to bleed pressure from a pressurized source.

The foregoing has outlined some of the more pertinent objects of the invention. These objects should be construed to be merely illustrative of some of the more prominent features and applications of the intended invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

The invention is defined by the appended claims with a specific embodiment shown in the attached drawings. For the purpose of summarizing the invention, the invention comprises a flow control valve for variably controlling the flow of a fluid therethrough. The invention further comprises a check valve incorporated within the flow control valve. The flow control valve having a check valve incorporated therein allows the valve to be used for inflating a tank or other container, such as a blood pressure ouff, to a pressurized state, with the check valve thereof functioning to maintain the pressure within the tank during pressurization and thereafter. The pressurized container may then be depressurized by bleeding the fluid therefrom upon variably opening the flow control valve from a closed position.

More particularly, the flow control valve of the invention comprises an integral body having a main axial fluid passageway with an input and an output. A check valve is positioned within the main fluid passageway allowing a fluid such as air, to flow from the input to the output while preventing the flow of air from the output to the input. The check valve may comprise a conventional check valve having a valve element freely reciprocatingly positioned therein which seats against a valve seat to prevent the flow of air from the output to the input. Alternatively, the check valve may comprise a check valve having a preset cracking pressure such as the check valve disclosed in U.S. Pat. Nos. 3,831,629, in U.S. patent application, Ser. No. 450,453, filed Dec. 16, 1982 now U.S. Pat. No. 4,602,655, or in the U.S. patent application entitled "Check Valve with Preset Cracking Pressure", Ser. No. 867,319, filed May 23, 1986, the disclosure of each of which is hereby incorporated by reference herein. The flow control valve further comprises a bleeder valve positioned within a bleeder passageway connected in fluid communication with the main fluid passageway and operable by means of a turn knob or cap. During use, upon rotation of the turn knob from a closed to a variably open position, the pressure contained within the tank is variably bled to the atmosphere via a vent hole.

All of the components of the flow control valve of the invention are manufactured from injection molding techniques and then simply assembled together by hand or by automatic assembly machines. The machining and deburring typically required by prior art flow control valves are eliminated. Thus, the flow control valve of the invention may be economically manufactured and assembled at significant cost savings when compared with prior art flow control valves.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 2:
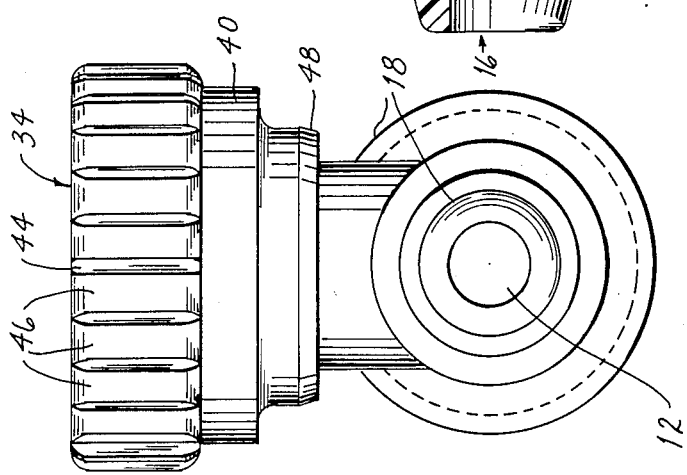
FIG. 2 is a left end view of the flow control valve of the invention of FIG. 1.

The flow control valve 10 of the invention comprises a bleed valve 10B and a check valve 10C. More particularly, valve 10 comprises an integral body 11 having main axial fluid passageway 12 with input 14 and output 16. As shown in FIG. 2, the main fluid passageway 12 preferably comprises a generally cylindrical configuration. A plurality of inwardly disposed barbs 18 are annularly positioned about the outside surface of the input 14 and output 16 of the main fluid passageway 12 to facilitate connection of a plastic tube to the input 14 and the output 16.

The body 11 of the flow control valve 10 further comprises a bleed fluid passageway 20 connected in fluid communication with the main fluid passageway 12. The cylindrical wall 22 of the bleed fluid passageway 20 comprises a large diameter portion 24 and a small diameter portion 26 joined together by means of a forwardly converging frustro-conical valve seat 28. The exterior surface of wall 22 of the bleed fluid passageway 20 comprises exterior threads 30. Finally, bleed hole 32 is formed through the large diameter portion 24 of wall 22 of the bleed fluid passageway 20.

Bleed knob or cap 34 is provided for threaded engagement over the opened end 36 of the large diameter portion 24 of the bleed fluid passageway 20. More particularly, bleed cap 34 comprises a generally circular configuration having a base portion 38 and annular wall portion 40. An internal thread 42 is formed along the lumen of the annular wall portion 40 for threaded engagement with the thread 30 of wall 22 of the bleed fluid passageway 20. The outside annular surface 44 of the bleed cap 34 may be provided with a plurality of knurled ridges 46 or the like to enhance gripping of the bleed cap 34 during use. Further, the annular wall portion 40 may include an inwardly crimped annular edge 48 to prevent the bleed cap 34 from being inadvertently completely unthreaded from the bleed fluid passageway 20 during use.

A bleed valve element or poppet 50 is reciprocatingly positioned within the bleed fluid passageway 20. The valve element 50 comprises a large diameter portion 52 and a small diameter portion 54 joined together by a forwardly converging frustro-conical valve seat 56 corresponding to the large diameter portion 24, small diameter portion 26 and valve seat 28 of the bleed fluid passageway 20. Hence, the valve element 50 is loosely positioned within the bleed fluid passageway 20 with the respective seats 28 and 56 sealingly engaging each other to form a fluid-tight seal between the seats 28 and 56 when the seat 56 of the element 50 is forced against the seat 28 of the bleed fluid passageway 20. Finally, the large diameter portion 52 of the valve element 50 preferably comprises a forwardly formed blind axial cylindrical hole 58 along the length thereof. A plurality of axially extending lands or ribs 60 are positioned exteriorly along the outside surface of the large diameter portion 52 of the valve element 50 to centrally locate the valve element 50 within the bleed fluid passageway 20.

The longitudinal length of the large diameter portion 52 is appreciably greater than the longitudinal length of the large diameter portion 24 of the bleed fluid passageway 20 such that the rearward edge 62 of the valve element 50 appreciably protrudes from the rearward edge 64 of the bleed fluid passageway 20 and is engagable by the inward surface 66 of the base portion 38 of the bleed cap 34. Consequently, it should be readily apparent that clockwise rotation of the bleed cap 34 increasingly causes its inward surface 66 to engage against the rearward edge 62 of the valve element 50, thereby increasingly forcing the valve element 50 into the bleed fluid passageway 20 and, in turn, increasingly forcing the seat 56 of the valve element 50 against the seat 28 of the bleed fluid passageway 20. It is noted that, as the seat 56 of the valve element 50 is increasingly forced against the seat 28 of the bleed fluid passageway 20, the sleeve formed by the hole 58 within the large diameter portion 52 of the element 50 increasingly flexes to a "wavy" configuration proportional to the amount of force exerted on the element 50 by the bleed cap 34. This function correspondingly increases the amount of sealing force present between the mated seats 56 and 28 until the bleed cap 34 is fully threaded onto the bleed fluid passageway 20. Moreover, it is noted that due to the flexing of the large diameter portion 52 of the element 50, the bleed cap 34 may be fully threaded onto the bleed fluid passageway 20 without damaging the mated seats 56 and 28.

During bleeding, the bleed cap 34 may be counter-rotated to reduce the sealing force between the mated seats 56 and 28 until the fluid begins to escape between the seats 56 and 28 and exits the valve 10 via bleed hole 32. Obviously, as the bleed cap 34 is increasingly unthreaded from the bleed fluid passageway 20, more bleeding will occur at an increased rate until the tank or other container is depressurized or until the bleed cap 34 is threaded onto the bleed fluid passageway 20 to reduce or completely stop bleeding.

Returning now to the check valve 10C of the flow control valve 10, the check valve 10C may comprise the check valve illustrated in U.S. Pat. No. 3,831,629, in U.S. patent application, Ser. No. 450,453 filed Dec. 16, 1982, now U.S. Pat. No. 4,602,655, or in U.S. patent application, entitled "Check Valve with Preset Cracking Pressure", Ser. No. 876,319, filed May 23, 1986, now U.S. Pat. No. 4,681,132, the disclosures of which are hereby incorporated by reference herein. Briefly summarizing the first two such disclosures, the check valve 10C of that type comprises a valve element 68 having a forwardly converging frustro-conical seat 70 positioned within a housing 72 correspondingly having a forwardly converging frustro-conical seat 74. The rearward end 76 of the housing 72 is folded inwardly at crimp 78 to oompressibly engage rearward edge 80 of the valve element 68 thereby forcibly engaging the seats 70 and 74 together to form an airtight seal capable of being opened at a predetermined cracking pressure exerted on the input of the check valve 10C either by fluid pressure or by a syringe or other instrument.

Figure 1:
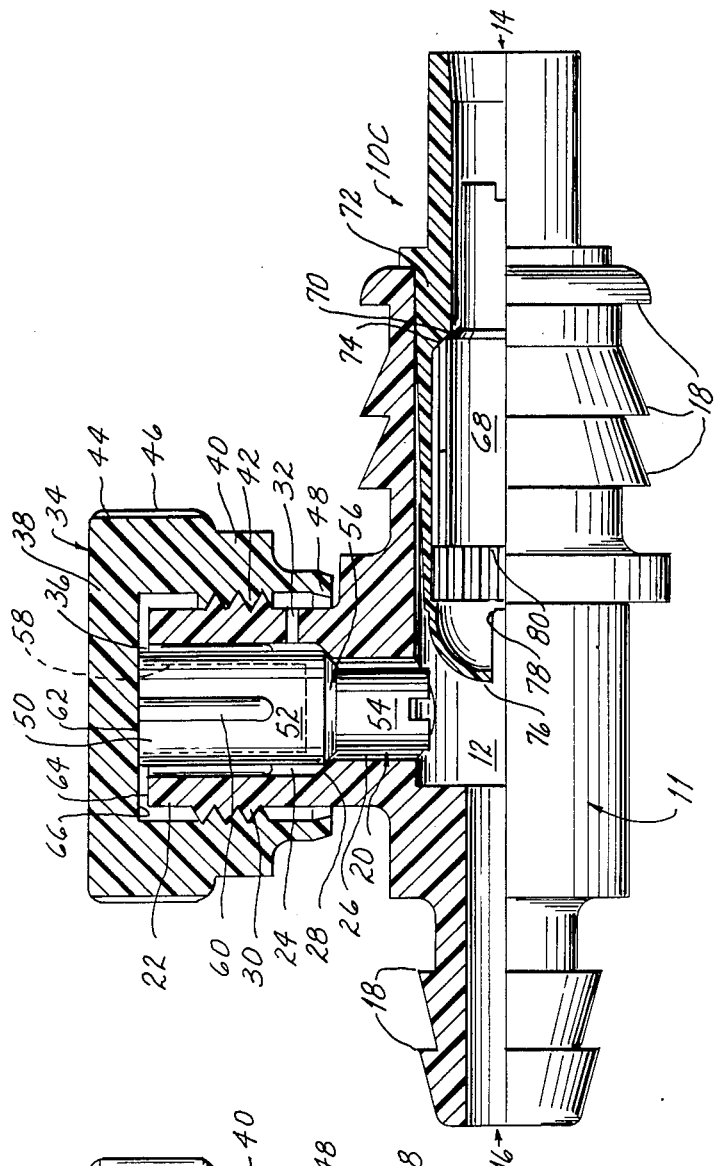
FIG. 1 is a partial cross-sectional view of the flow control valve of the invention.

Alternatively, however, check valve 10C may comprise a check valve having no cracking pressure in which the valve element 68 is loosely reciprocatingly positioned within the housing 72 such that the rearward crimp 78 reciprocatingly retains the valve element 68 within housing 72 but does not exert a compressive force on the valve element 68 (see FIG. 1).

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit of the invention.

Now that the invention has been described,
What is claimed is:

1. A flow control valve, comprising in combination:
   (a) a one piece, integral body having an integral bleed fluid passageway and an integral axial fluid passageway, said fluid passageways each having an input and an output, said output of said bleed fluid passageway being connected in fluid communication with said output of said axial fluid passageway, said bleed fluid passageway including a large diameter portion and a small portion joined together at a bleed valve seat means, said bleed valve seat means comprising a forward converging frustro-conical valve seat;
   (b) a one piece bleed cap threadably engaging about said input of said bleed fluid passageway;
   (c) a one piece bleed valve element reciprocatingly positioned within said bleed fluid passageway, said bleed valve element comprising a large diameter portion formed with an internal hole with external ribs to thereby constitute a flexible sleeve and a small diameter portion and an element valve seat means positioned therebetween for sealing engagement with said bleed valve seat means of said bleed fluid passageway, said bleed valve element being dimensioned to protrude from said input of said bleed fluid passageway to be engaged by an inner surface of said bleed cap such that, upon further movement of said bleed cap about said bleed fluid passageway, said bleed valve element is flexed about its hole end, said element valve seat means of said valve element is forced into sealing engagement with said bleed valve seat means of said bleed fluid passageway, a bleed hole formed through said large diameter portion of said bleed fluid passageway allowing air to bleed therethrough into said axial fluid passageway upon unseating of said valve seat means of said valve element from said bleed valve seat means of said bleed fluid passageway; and
   (d) a check valve positioned within said input of said axial fluid passageway and oriented to prevent fluid flow from said output of said axial fluid passageway to said input of said axial fluid passageway, said check valve comprising
      (i) a valve housing and
      (ii) a valve element reciprocatingly positioned within said valve housing, said valve element and said valve housing having mating forwardly converging frustro-conical seats which form a fluid tight seal therebetween when fluid back pressure is exerted on said valve element of said check valve, said valve housing being dimensioned to be sealingly inserted within said input of said axial fluid passageway allowing said check valve to be removed from said input of said axial fluid passageway.

2. The flow control valve as set forth in claim 1, wherein a lowermost edge of said bleed cap is formed inwardly to prevent said bleed cap from being completely unthreaded from said bleed fluid passageway.

3. The flow control valve as set forth in claim 1, wherein a plurality of annular barbs are formed on the outside surface of said axial fluid passageway allowing a tube to be connected to said input and said output thereof.

* * * * *